United States Patent
Ionkin

(10) Patent No.: US 7,371,879 B2
(45) Date of Patent: May 13, 2008

(54) BIVALENT MONOMERIC PHENOXY TIN COMPOUNDS

(75) Inventor: Alex Sergey Ionkin, Kennett Square, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/407,009

(22) Filed: Apr. 18, 2006

(65) Prior Publication Data

US 2007/0244325 A1 Oct. 18, 2007

(51) Int. Cl.
*C07F 7/00* (2006.01)
(52) U.S. Cl. .................................. 556/81
(58) Field of Classification Search ............... 556/81
See application file for complete search history.

(56) References Cited

FOREIGN PATENT DOCUMENTS

GB 993004 * 5/1965

OTHER PUBLICATIONS

B. Cetinkaya et al., J. Am. Chem. Soc. (1980) 102(6), 2088-9.*

* cited by examiner

*Primary Examiner*—Porfirio Nazario-Gonzalez

(57) ABSTRACT

The present invention relates to monomeric bivalent phenoxy tin compounds, processes for making the phenoxy tin compounds, and processes for making polyurethanes using the tin compounds as polymerization catalysts.

9 Claims, No Drawings

BIVALENT MONOMERIC PHENOXY TIN COMPOUNDS

FIELD OF THE INVENTION

The present invention relates to bivalent tin compounds. The compounds are stabilized by phenoxy groups with bulky ortho-substituents and are suitable for use as catalysts for polymerization, primarily for polyurethane polymerization.

BACKGROUND

Coating manufacturers have achieved significant progress in developing novel components for polyurethanes to improve coating properties, although less effort has been put into the search for novel catalyst systems. The usual catalysts for this process are dibutyltindilaurate and tertiary amines. Dialkyl and trialkyltin derivatives, classes of the compounds to which dibutyltindilaurate belongs to, have been discussed as having some issues regarding human toxicity. See, for example, Boyer, I. J., *Toxicology*, 1989, 55, 253 and Lytle, T. F.; Manning, C. S.; Walker, W. W.; Lytle, J. S.; Page, D. S., *Appl. Organomet. Chem.*, 2003, 17, 653. Divalent tin compounds as disclosed herein, which do not have alkyl-tin bonds, have been tested as catalysts for polyurethane formation.

Organometallics of the group 14 elements, particularly dibutyltin derivatives, are known to catalyze transesterification, transcarbamoylation and urethane formation. While there has been progress in developing novel components for polyurethanes to improve coating properties, a need remains for novel catalyst systems. Known catalysts for forming polyurethanes include dibutyltindilaurate and tertiary amines. Dialkyl and trialkyltin derivatives, classes of the compounds to which dibutyltindilaurate belongs, have some toxicity to humans, so less toxic catalysts are desired.

Jousseaume, B. et al., ("Air Activated Organotin Catalysts for Silicone Curing and Polyurethane Preparation" (1994) Organometallics 13:1034), and Bernard, J. M. et al. (U.S. Pat. No. 6,187,711) describe the use of distannanes as latent catalysts, e.g. $Bu_2(AcO)SnSn(OAc)Bu_2$.

B. Cetinkaya, et al., J. Am. Chem. Soc. (1980), 102(6), 2088-9, disclose bivalent germanium, tin, and lead 2,6-di-tert-butylphenoxides and the crystal and molecular structures of $M(OC_6H_2Me-4-But2-2,6)_2$, where M is Ge or Sn.

Co-pending and co-owned U.S. Pat. Applications (CL-3193, CL-3280, CL3191), all incorporated by reference in their entirety, disclose divalent and quadrivalent tin and germanium compounds and their use as catalysts. (CL-3193) describe quadrivalent derivatives of tin and germanium and their use as catalysts. (CL-3280) describes divalent tin and germanium compounds stabilized by bulky chelating P^O ligands.

SUMMARY OF THE INVENTION

The present invention relates, in some embodiments, to a compound of the formula:

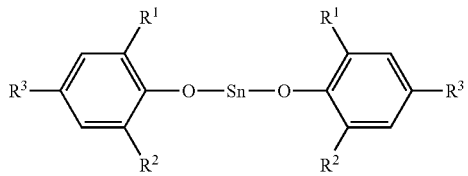

wherein
each $R^1$ and $R^2$ are each independently a sterically hindering group; and
each $R^3$ is independently a group that enables solubility of the compound;

DETAILED DESCRIPTION

In one embodiment, the present invention provides bivalent tin compounds and processes for making the compounds. In some embodiments, the invention provides processes for urethane polymerization wherein the bivalent tin compounds are used as catalysts.

Because phenoxytin(II) compounds do not contain direct tin-carbon bonds (e.g., tin-butyl groups in the majority of cases), they are expected to have lower human toxicity. It is believed that the ortho-tert-butyl substituted phenoxy groups are less toxic to humans. It has been discovered that phenoxytin(II) compounds are useful as catalysts for the polymerization of alcohols and isocyanates to form polyurethane polymers.

The compounds comprise sterically hindered groups. These groups are generally "bulky", as the term is used and well-known to those skilled in the art, and the term "sterically hindered", as used herein, refers to compounds having a spatial arrangement of their atoms such that a given reaction with another molecule is prevented or retarded. For example, a sterically hindered group can prevent the dimerization or oligomerization of two-coordinated tin atom, and thus will allow tin atom to be divalent and two-coordinated. Non-limiting examples of sterically hindered groups are tert-butyl, triethylmethyl, triphenylmethyl (Trityl), 1-methylcyclohexyl, 1-methylcyclopentyl, neopentyl, trimethylsilyl, triphenylsilyl, tert-butyldimethylsilyl, tris(trimethylsilyl)silyl, trifluoromethyl, adamantyl, methyladamantyl, di-tert-butyl-phosphino, di-tert-butyl-thiophosphino, di-tert-butyl-phosphoryl, di-tert-butyl-iminophosphino, di-mesityl-phosphino, di-mesityl-thiophosphino, di-mesityl-phosphoryl, di-mesityl-iminophosphino, tert-butyl-amino, tert-butyl-thio, tert-butyl-seleno, tert-butoxy, di-tert-butyl-boronyl; mesityl, 2,4,6-tri-iso-propylphenyl, 2,4,6-tri-ethylphenyl, 2,4,6-tri-tert-butylphenyl, 2,4,6-tri-phenylphenyl, pyrenyl, anthracenyl, acridinyl, and xanthenyl.

Also provided in the present invention are compounds of the formula

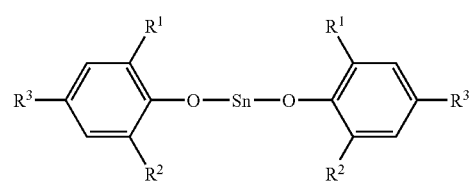

wherein
each $R^1$ and $R^2$ are each independently a sterically hindering group; and
each $R^3$ is independently a group that enables solubility of the compound.

More specifically, some embodiments of the present invention include a compound of the formula

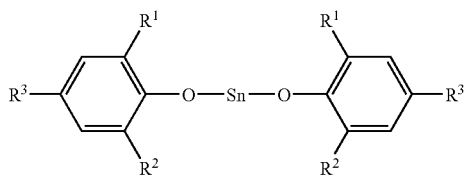

wherein each $R^1$ and $R^2$ sterically hindering group is selected from the group consisting of trialkyl, heteroaryl, phenyl, substituted phenyl, polyaromatic, fused aromatic systems, heteroaromatic, phosphines, and C-4 to C-20 tertiary alkyls, with the proviso that at most one $R^1$ and $R^2$ is tert-butyl.

Additionally provided is a process for forming bivalent tin compounds disclosed herein, comprising mixing a substituted phenol and a monomeric bis(triorganosilyl)amido tin (II) material in the presence of a solvent to form the bivalent tin compound.

Generally, the production of the compounds herein described begins by mixing a substituted phenol (e.g., 2,4,6-Tri-tert-butyl-phenol) and a monomeric bis(triorganosilyl) amido tin(II) material (e.g., bis[bis(trimethylsilyl)amino]tin (II)) in the presence of a solvent (typically toluene, but any convenient solvent known to those skilled in the art can be used) to form a bivalent tin compound (e.g., 2,4,6-Tri-tert-butylphenoxide of Sn(II)). The compound is generally isolated after solvent and other volatiles are removed, and the residue recrystallized.

To form polyurethanes using the compounds as catalysts, the compounds are combined with appropriate solvents, one or more alcohols or polyols, and one or more isocyanates, to form a mixture. The gel time of the mixture is measured. The so-called "gel time" corresponds to the time in hours following activation of the catalyst at which flow is no longer observed in the mixture. The results of the application of the novel divalent tin compounds disclosed herein in the catalytic formation of polyurethanes are shown in the Tables in the Examples below. Polyurethanes formed using the compounds and processes disclosed herein generally have gel times longer than those of polyurethanes formed using conventional catalysts. Generally, an increase in gel time of 0.8 to 8.0 hours is achieved when the compounds disclosed herein are use in the process disclosed in the Examples below. The gel time of a polyurethane made using the catalysts and processes disclosed herein depends, in part, upon the concentration of the catalyst. Preferred concentrations of catalyst are from 1800 to 250 ppm (based on the total amount of materials reacted. Thus, a gel time can be controlled by the amount of catalyst used.

Catalytic activity can also be shown by testing of film dry time. As shown in the Examples below, a thin film test was done using a B. K. Dry Time Recorder (Gardco Model BK-3, Pompano, Fla.) to determine how long it takes for the film to completely dry. There are four stages in the drying phase that can be measured with the use of a B. K. strip. The first stage indicates the time it takes for the solvent to evaporate from the sample. The end of the first stage is found where a pear shaped impression is formed in the film. The second phase corresponds to a solution-gel transition. The second stage is identified when the needle cuts a continuous track in the film. The third phase shows the time it takes for the surface to dry. This stage begins when there are small interruptions in the track the needle is forming. Stage four shows the time it takes for the film to completely dry. Stage four is when the needle does not penetrate the film any longer but rides on the top.

The production of polyurethane is usually achieved by addition of polymeric polyols to isocyanates. Polyols are generally defined as polymeric or oligomeric organic species with at least two hydroxy functionalities. A schematic of a polyol generally used in the art is shown below as structure 7, and is referred to as Polyol herein. It is available from DuPont, Wilmington, Del.

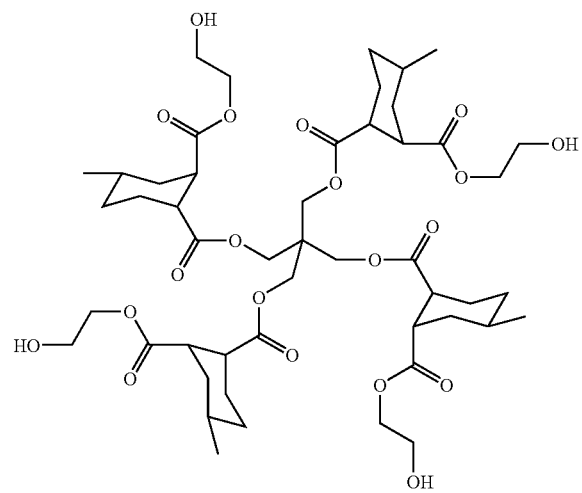

The starting Polyol may be either a low molecular weight oligomer (generally from about 500 to 3000 wt. avg. molecular weight, preferably from about 600 to about 2000 wt. avg. molecular weight) or a polymer with OH functionality (generally from about 2000 to about 300,000 wt. avg. molecular weight, preferably from about 2500 to about 100,000 wt. avg. molecular weight, and more preferably from about 2500 to about 50,000 wt. avg. molecular weight.

The production of a polyurethane may also use other isocyanate-reactive compounds, including but not limited to alcohols, amines, thiols and mixtures of these compounds.

An example of an isocyanate with functional groups capable of reacting with hydroxyl is as follows:

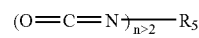

wherein $R_5$ is an alkyl structure such as, for example, ethyl, propyl, phenyl. In some preferred embodiments, $R_5$ is $(CH_2)_6$. The formula directly hereinabove represents a "polyisocyanate" since n>2.

Examples of suitable isocyanates include aromatic, aliphatic or cycloaliphatic di-, tri- or tetra-isocyanates, including polyisocyanates having isocyanurate structural units, such as, the isocyanurate of hexamethylene diisocyanate and isocyanurate of isophorone diisocyanate; the adduct of 2 molecules of a diisocyanate, such as, hexamethylene diisocyanate and a diol such as, ethylene glycol; uretidiones of hexamethylene diisocyanate; uretidiones of isophorone diisocyanate or isophorone diisocyanate; the adduct of trimethylol propane and meta-tetramethylxylene diisocyanate.

Additional examples of suitable polyisocyanates include 1,2-propylene diisocyanate, trimethylene diisocyanate, tetramethylene diisocyanate, 2,3-butylene diisocyanate, hexamethylene diisocyanate, octamethylene diisocyanate, 2,2, 4-trimethyl hexamethylene diisocyanate, 2,4,4-trimethyl hexamethylene diisocyanate, dodecamethylene diisocyanate, omega, omega-dipropyl ether diisocyanate, 1,3-cyclopentane diisocyanate, 1,2-cyclohexane diisocyanate, 1,4-cyclohexane diisocyanate, isophorone diisocyanate, 4-methyl-1,3-diisocyanatocyclohexane, trans-vinylidene diisocyanate, dicyclohexylmethane-4,4'-diisocyanate, 3,3'-dimethyl-dicyclohexylmethane4,4'-diisocyanate, a toluene diisocyanate, 1,3-bis(1-isocyanato1-methylethyl)benzene, 1,4-bis(1-isocyanato-1-methylethyl)benzene, 1,3-bis(isocyanatomethyl)benzene, xylene diisocyanate, 1,5-dimethyl-2, 4-bis(isocyanatomethyl)benzene, 1,5-dimethyl-2,4-bis(2-isocyanatoethyl)benzene, 1,3,5-triethyl-2,4-bis (isocyanatomethyl)benzene, 4,4'-diisocyanatodiphenyl, 3,3'-dichloro-4,4'-diisocyanatodiphenyl, 3,3'-diphenyl-4,4'-diisocyanatodiphenyl, 3,3'-dimethoxy-4,4'-diisocyanatodiphenyl, 4,4'-diisocyanatodiphenylmethane, 3,3'-dimethyl-4,4'-diisocyanatodiphenyl methane, a diisocyanatonaphthalene, polyisocyanates having isocyanaurate structural units, the adduct of 2 molecules of a diisocyanate, such as, hexamethylene diisocyanate or isophorone diisocyanate, and a diol such as ethylene glycol, the adduct of 3 molecules of hexamethylene diisocyanate and 1 molecule of water (available under the trademark Desmodur® N from Bayer Corporation of Pittsburgh, Pa.), the adduct of 1 molecule of trimethylol propane and 3 molecules of toluene diisocyanate (available under the trademark Desmodur® L from Bayer Corporation), the adduct of 1 molecule of trimethylol propane and 3 molecules of isophorone diisocyanate, compounds such as 1,3,5-triisocyanato benzene and 2,4,6-triisocyanatotoluene, and the adduct of 1 molecule of pentaerythritol and 4 molecules of toluene diisocyanate.

A specific example of an isocyanate capable of reacting with hydroxyl groups is Desmodur® 3300 isocyanate, available from Bayer. Desmodur® 3300 as available commercially, comprises a mixture of compounds, with a general structure as follows (also, pentamer, heptamer and higher molecular weight species can be present):

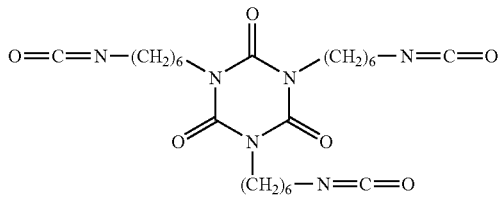

It is preferred that the compositions made before mixing with the inventive compound(s) be of relatively low molecular weight (generally less than about 50,000 wt. avg. molecular weight so as to keep the viscosity of the compositions before crosslinking low, and therefore avoid or minimize the need for solvent(s).

Other materials, which may be present in the compositions and processes, include one or more solvents (and are meant to act only as solvents). These preferably do not contain groups such as hydroxyl or primary or secondary amino.

The polyurethanes and the process for making them are useful as encapsulants, sealants, and coatings, especially transportation (automotive) and industrial coatings. As transportation coatings, the present compositions are useful as both OEM (original equipment manufacturer) and automotive refinish coatings. They may also be used as primer coatings. They often cure under ambient conditions to tough hard coatings and may be used as one or both of the so-called base coat and clear coat automotive coatings. This makes them particularly useful for repainting of transportation vehicles in the field.

Depending on use, the compositions and the materials used in the present processes may contain other materials. For example, when used as encapsulants and sealants, some compositions may contain fillers, pigments, and/or antioxidants. The compositions can be used as catalysts for making polyurethanes for coatings and generally in applications where curing of polyurethane is required, for example in the adhesives industry and related applications. The compositions are also suitable for use as clear or pigmented coatings in industrial and maintenance coating applications.

When used as coatings, polyurethanes made using the present compositions contain typical additives and other ingredients known in the art, some examples of which are recited below without intent to limit the compositions thereto. In particular there may be other polymers (especially of low molecular weight, "functionalized oligomers") which are either inert, or have functional group(s) other than hydroxyl or isocyanate and can also react with other reactive materials in the coating composition.

Representative of the functionalized oligomers that can be employed as components or potential crosslinking agents of the coatings are the following:

Hydroxyl oligomers: The reaction product of multifunctional alcohols such as pentaerythritol, hexanediol, trimethylol propane, with cyclic monomeric anhydrides such as hexahydrophthalic anhydride, methylhexahydrophthalic anhydride, produce acid oligomers These acid oligomers are further reacted with monofunctional epoxies such as butylene oxide, propylene oxide, to form hydroxyl oligomers.

Silane oligomers: The above hydroxyl oligomers further reacted with isocyanato propyltrimethoxy silane.

Epoxy oligomers: The diglycidyl ester of cyclohexane dicarboxylic acid, such as Araldite® CY-184 from Ciba Geigy, and cycloaliphatic epoxies, such as ERL®-4221, from Union Carbide.

Aldimine oligomers: The reaction product of isobutyraldehyde with diamines such as isophorone diamine.

Ketimine oligomers: The reaction product of methyl isobutyl ketone with diamines such as isophorone diamine.

Melamine oligomers: Commercially available melamines such as CYMEL® 1168 from Cytec Industries.

AB-Functionalized oligomers: Acid/hydroxyl functional oligomers made by further reacting the above acid oligomers with 50%, based on equivalents, of monofunctional epoxy such as butylene oxide or blends of the hydroxyl and acid oligomers mentioned above or any other blend depicted above.

CD-Functionalized crosslinkers: Epoxy/hydroxyl functional crosslinkers such as the polyglycidyl ether of Sorbitol DCE-358® from Dixie Chemical or blends of the hydroxyl oligomers and epoxy crosslinkers mentioned above or any other blend as depicted above.

The coatings may additionally contain a binder of a noncyclic oligomer, i.e., one that is linear or aromatic. Such noncyclic oligomers can include, for instance, succinic anhydride- or phthalic anhydride-derived moieties in hydroxyl oligomers.

Preferred functionalized oligomers have weight average molecular weights not exceeding about 3,000 with a polydispersity not exceeding about 1.5; more preferred oligomers have molecular weights not exceeding about 2,500 and a polydispersity not exceeding about 1.4; most preferred oligomers have molecular weights not exceeding about 2,200, and a polydispersity not exceeding about 1.25. Other additives that can be present include polyaspartic esters, which are the reaction product of diamines, such as, isopherone diamine with dialkyl maleates, such as, diethyl maleate.

The coating compositions may be formulated as high solids coating systems dissolved in at least one solvent. The solvent is usually organic. Preferred solvents include aromatic hydrocarbons such as petroleum naphtha or xylenes; ketones such as methyl amyl ketone, methyl isobutyl ketone, methyl ethyl ketone or acetone; esters such as butyl acetate or hexyl acetate; and glycol ether esters such as propylene glycol monomethyl ether acetate.

The coating compositions can also contain a binder of an acrylic polymer of weight average molecular weight greater than 3,000, or a conventional polyester such as SCD®-1040 from Etna Product Inc. for improved appearance, sag resistance, flow and leveling and such. The acrylic polymer can comprise monomers such as acrylates, methacrylates, and styrene and optionally functional monomers such as hydroxy ethyl acrylate, glycidyl methacrylate, and gamma methacrylylpropyl trimethoxysilane.

The coating compositions can also contain a binder of a dispersed acrylic component which is a polymer particle dispersed in an organic media, which particle is stabilized by what is known as steric stabilization. Hereinafter, the dispersed phase or particle, when sheathed by a steric barrier, will be referred to as the "macromolecular polymer" or "core". The stabilizer forming the steric barrier, attached to the core, will be referred to as the "macromonomer chains" or "arms".

The dispersed polymer contains about 10 to 90%, preferably 50 to 80%, by weight, based on the weight of the dispersed polymer, of a high molecular weight core having a weight average molecular weight of about 50,000 to 500,000. The preferred average particle size is 0.1 to 0.5 microns. The arms, attached to the core, make up about 10 to 90%, preferably 10 to 59%, by weight of the dispersed polymer, and have a weight average molecular weight of about 1,000 to 30,000, preferably 1,000 to 10,000. The macromolecular core of the dispersed polymer is comprised of polymerized acrylic monomer(s) optionally copolymerized with ethylenically unsaturated monomer(s). Suitable monomers include styrene, alkyl acrylate or methacrylate, ethylenically unsaturated monocarboxylic acid, and/or silane-containing monomers. Such monomers as methyl methacrylate contribute to a high Tg (glass transition temperature) dispersed polymer, whereas such "softening" monomers as butyl acrylate or 2-ethylhexylacrylate contribute to a low Tg dispersed polymer. Other optional monomers are hydroxyalkyl acrylates or methacrylates or acrylonitrile. Optionally, the macromolecular core can be crosslinked through the use of diacrylates or dimethacrylates such as allyl methacrylate or post reaction of hydroxyl moieties with polyfunctional isocyanates. The macromonomer arms attached to the core can contain polymerized monomers of alkyl methacrylate, alkyl acrylate, each having 1 to 12 carbon atoms in the alkyl group, as well as glycidyl acrylate or glycidyl methacrylate or ethylenically unsaturated monocarboxylic acid for anchoring and/or crosslinking. Typically useful hydroxy-containing monomers are hydroxy alkyl acrylates or methacrylates as described above.

The coating compositions can also contain conventional additives such as pigments, stabilizers, rheology control agents, flow agents, toughening agents and fillers. Such additional additives will, of course, depend on the intended use of the coating composition. Fillers, pigments, and other additives that would adversely affect the clarity of the cured coating may not typically be included if the composition is intended as a clear coating.

The coating compositions are typically applied to a substrate by conventional techniques such as spraying, electrostatic spraying, roller coating, dipping or brushing. The present formulations are particularly useful as a clear coating for outdoor articles, such as automobile and other vehicle body parts. The substrate is generally prepared with a primer and or a color coat or other surface preparation prior to coating with the present compositions.

A layer of a coating composition is cured under ambient conditions in the range of 30 minutes to 24 hours, preferably in the range of 30 minutes to 3 hours to form a coating on the substrate having the desired coating properties. One of skill in the art appreciates that the actual curing time depends upon the thickness of the applied layer and on any additional mechanical aids, such as, fans that assist in continuously flowing air over the coated substrate to accelerate the cure rate. If desired, the cure rate may be further accelerated by baking the coated substrate at temperatures generally in the range of from about 60° C. to 150° C. for a period of about 15 to 90 minutes. The foregoing baking step is particularly useful under OEM (Original Equipment Manufacture) conditions.

A polyurethane composition made using the compounds disclosed herein as catalysts is suitable for providing coatings on a variety of substrates, particularly for providing clear coatings in automotive OEM or refinish applications typically used in coating auto bodies. The coating composition can be formulated in the form of a clear coating composition, pigmented composition, metallized coating composition, basecoat composition, monocoat composition or a primer. The substrate is generally prepared with a primer and or a color coat or other surface preparation prior to coating with the present compositions.

Suitable substrates that can be coated with a coating comprising a polyurethane as disclosed herein include automobile bodies, items manufactured and painted by automobile sub-suppliers such as, for example, frame rails, commercial trucks and truck bodies, including but not limited to beverage bodies, utility bodies, ready mix concrete delivery vehicle bodies, waste hauling vehicle bodies, and fire and emergency vehicle bodies, as well as potential attachments or components to such truck bodies, buses, farm and construction equipment, truck caps and covers, commercial trailers, consumer trailers, recreational vehicles, including but not limited to, motor homes, campers, conversion vans, vans, pleasure vehicles, pleasure craft snow mobiles, all terrain vehicles, personal watercraft, motorcycles, bicycles, boats, and aircraft. Other substrates that can be coated include industrial and commercial new construction and maintenance thereof; cement and wood floors; walls of commercial and residential structures, such office buildings and homes; amusement park equipment; concrete surfaces, such as parking lots and drive ways; asphalt and concrete road surface, wood substrates, marine surfaces; outdoor structures, such as bridges, towers; coil coating; railroad cars; printed circuit boards; machinery; OEM tools; signage; fiberglass structures; sporting goods; golf balls; and sporting equipment.

EXAMPLES

Example 1

2,4,6-Tri-tert-butylphenoxide of Sn(II)

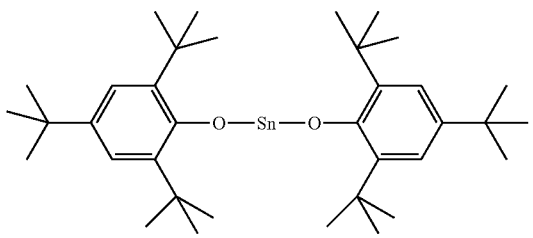

20.14 g (0.0767 mol) of 2,4,6-Tri-tert-butyl-phenol, 16.86 g (0.0384 mol) of bis[bis(trimethylsilyl)amino]tin(II) and 100 ml of toluene were stirred at room temperature under nitrogen for 24 hours. Then, the solvent and bis(trimethylsilyl)amine was removed in 1 mm vacuum. The residue was recrystallized from 50 ml of pentane. Yield of 2,4,6-tri-tert-butylphenoxide of Sn(II) was 17.34 g (70%) as an orange solid, which is unstable on air. $^1$H NMR ($C_6D_6$) 1.30 (s, 18H, t-Bu), 1.52 (s, 36H, t-Bu), 7.43 (s, 4H, arom-H). $^{13}$C NMR ($C_6D_6$) 32.1, 33.2, 34.7, 35.6, 122.1, 139.1, 140.6, 155.9. $^{119}$Sn NMR ($C_6D_6$)–191.1 ppm. Structure was proven by X-ray analysis.

Example 2

2,6-Di-tert-butyl-4-methoxy-phenoxide of Sn(II)

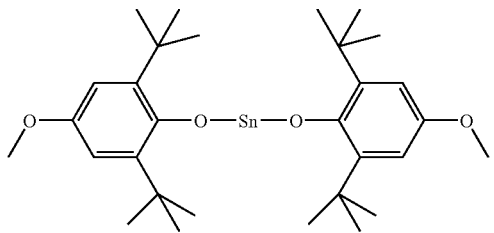

15.0 g (0.0635 mol) of 2,6-Di-tert-butyl-4-methoxy-phenol, 14.64 g (0.0333 mol) of bis[bis(trimethylsilyl)amino]tin(II) and 100 ml of toluene were stirred at room temperature under nitrogen for 24 hours. Then, the solvent and bis(trimethylsilyl)amine was removed in 1 mm vacuum. The residue was recrystallized from 50 ml of pentane. Yield of 2,6-di-tert-butyl-4-methoxy-phenoxide of Sn(II) was 14.3 g (77%) as an orange solid, which is unstable on air. $^1$H NMR ($C_6D_6$) 1.60 (s, 36H, t-Bu), 3.59 (s, 6H, MeO), 7.12 (s, 4H, arom-H). $^{13}$C NMR ($C_6D_6$) 33.0, 35.5, 55.4, 111.4, 140.5, 151.9, 152.8. Structure was proven by X-ray analysis as shown in FIG. 1.

Example 3

Gel Time Testing of Sn(2,4,6tri-tert-$Bu_3C_6H_2O$)$_2$:

A 2%, by mass, stock solution of catalyst prepared as in Example 1 was prepared by taking 116 mg of catalyst then diluting it with butyl acetate until it reached a total mass of 5.799 g. Two samples were prepared, one at 800 ppm and the other at 1800 ppm. The standard starting reagents for doing a gel time test or a B. K. Dry test was 1.95 g of Desmodur® 3300A and 4.74 g Polyol. For the 800 ppm solution 197 µl of stock solution was added to this mixture, for the 1800 ppm solution 443 µl of stock solution was added using a pipette. Three more samples were also ran later at different concentrations using the same amount of Desmodur® 3300A and Polyol. These samples were at 1200 ppm, 500 ppm, and 250 ppm using 295 µl, 123 µl, 61.6 µl of stock solution respectively. The gel times for these samples are listed in the table below.

TABLE 1

Gel times of polyurethanes with 2,4,6-tri-tert-butylphenoxide of Sn(II): Sn(2,4,6 $^t$Bu$_3$C$_6$H$_2$O)$_2$. Increasing the catalyst loadings resulted in shortening of gel times.

| Concentration (ppm) | Gel Time (hours) |
|---|---|
| 250 | 8.23 |
| 500 | 3.27 |
| 800 | 1.65 |
| 1200 | 1.28 |
| 1800 | .82 |

A B. K. dry time test was performed on the 800 ppm sample. The time scale setting on the machine was adjusted so that it would take 24 hours for the needle to traverse the whole strip. The film was applied to the B. K. strip using a 150 micron drawdown. The machine was turned on and the strip was placed in the machine and the needle was applied to the strip. The starting point of the needle on the strip was marked so that the times of the different stages could be measured and calculated. The distance on the strip between the starting point and the end of the previous stage are measured in centimeters, i.e. the distance from the start point to the end of stage three is used to calculate how long it took to reach stage four. Then the distance was multiplied by the constant for the 24 hour setting, 47.24 minutes. Stage three was reached after 8.7 hours, while stage four was reached after 12.4.

Example 4

Gel Time Testing of Sn(2,6 tBu$_2$ 4-methoxy $C_6H_2O$)$_2$

A 5%, by mass, stock solution of the catalyst prepared as in Example 2 was prepared by taking 101 mg of catalyst then diluting it with tetrahydrofuran until it reached a total mass of 2.001 g. Four samples were prepared at 1200 ppm, 800 ppm, 500 ppm, and 300 ppm. The standard starting reagents for doing a gel time test is 1.95 g of Desmodur® 3300A and 4.74 g Polyol were used. All stock solution aliquots were added using a pipette. The 1200 ppm solution was prepared by adding 118.4 µl to the Desmodur® and Polyol mixture. For the 800 ppm solution 78.9 µl of stock solution were added to this mixture. The 500 ppm solution was prepared with 49.3 µl of stock solution. The 300 ppm sample was prepared by adding 24.6 µl to the mixture. The gel times for these samples are listed on the table below.

TABLE 2

Gel times of polyurethanes with 2,6-di-tert-butyl-4-methoxy-phenoxide of Sn(II): Sn(2,6-tert-Bu$_2$-4-methoxy $C_6H_2O$)$_2$. Increasing the catalyst loadings resulted in shortening of gel times.

| Concentration (ppm) | Gel Time (hrs) |
|---|---|
| 1200 | 1.62 |
| 800 | 2.17 |
| 500 | 3.67 |
| 300 | 5-7 |

What is claimed is:

1. A compound of the formula:

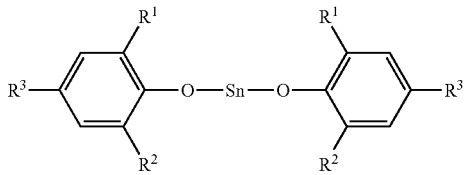

wherein
- each $R^1$ and $R^2$ are each independently a sterically hindering group selected from the group consisting of trimethylsilyl, heteroaryl, phenyl, substituted phenyl, polyaromatic, fused aromatic systems, heteroaromatic, phosphines, and heteroaromatic; and
- each $R^3$ is independently a group that enables solubility of the compound.

2. The compound of claim 1, wherein said sterically hindering group is selected from the group consisting of triphenylmethyl (Trityl), triphenylsilyl, tert-butyldimethylsilyl, tris(trimethylsilyl)silyl, di-tert-butyl-phosphino, di-tert-butyl-thiophosphino, di-tert-butyl-phosphoryl, di-tert-butyl-iminophosphino, di-mesityl-phosphino, di-mesityl-thiophosphino, di-mesityl-phosphoryl, di-mesityl-iminophosphino, tert-butyl-amino, tert-butyl-thio, tert-butyl-seleno, tert-butoxy, di-tert-butyl-boronyl; mesityl, 2,4,6-tri-iso-propylphenyl, 2,4,6-tri-ethylphenyl, 2,4,6-tri-tert-butylphenyl, 2,4,6-tri-phenylphenyl, pyrenyl, anthracenyl, acridinyl, and xanthenyl.

3. The compound of claim 1, wherein each $R^3$ group is selected from the group consisting of triorganylsilyl, and phenyl.

4. The compound of claim 1, wherein each $R^3$ is methoxy.

5. A process for forming a bivalent monomeric tin compound comprising: mixing a substituted phenol and a monomeric tin(II) compound in the presence of a solvent to form the bivalent tin compound.

6. The process of claim 5, wherein the bivalent tin compound is of the formula

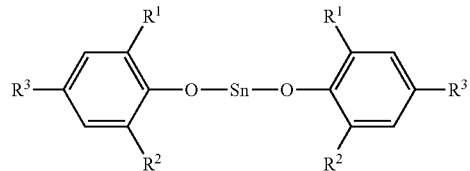

wherein
- each $R^1$ and $R^2$ are each independently a sterically hindering group selected from the group consisting of trimethylsilyl, heteroaryl, phenyl, substituted phenyl, polyaromatic, fused aromatic systems, heteroaromatic, phosphines, and heteroaromatic; and
- each $R^3$ is independently a group that enables solubility of the bivalent tin compound.

7. The process of claim 5 wherein the substituted phenol is 2,4,6-Tri-phenylphenol.

8. The process of claim 5 wherein the monomeric tin(II) compound is 2-tert-Butyl-6-phenyl-4-methoxy-phenoxide of Sn(II).

9. The process of claim 5 wherein the bivalent tin compound is 2,4,6-Tri-trimethylsilylphenoxide of Sn(II).

* * * * *